United States Patent
Löser

(10) Patent No.: US 6,402,046 B1
(45) Date of Patent: Jun. 11, 2002

(54) ULTRASONIC ATOMIZER

(75) Inventor: Ralf Löser, Lübeck (DE)

(73) Assignee: Drager Medizintechnik GmbH (DE)

( * ) Notice: Subject to any disclaimer, the term of this patent is extended or adjusted under 35 U.S.C. 154(b) by 0 days.

(21) Appl. No.: 09/577,183

(22) Filed: May 23, 2000

(30) Foreign Application Priority Data

Dec. 23, 1999 (DE) .......................... 199 62 280

(51) Int. Cl.$^7$ .............................................. B05B 17/04
(52) U.S. Cl. .................. 239/4; 239/102.1; 239/102.2; 128/200.16
(58) Field of Search ................... 239/102.1, 102.2, 239/4; 128/200.14, 200.16

(56) References Cited

U.S. PATENT DOCUMENTS

| | | | | |
|---|---|---|---|---|
| 3,690,317 A | * | 9/1972 | Millman | 239/102.2 |
| 3,828,773 A | * | 8/1974 | Buch et al. | 239/102.2 |
| 5,063,922 A | * | 11/1991 | Hakkinen | 128/200.16 |
| 5,361,989 A | * | 11/1994 | Merchat et al. | 239/102.2 |
| 5,551,416 A | * | 9/1996 | Stimpson et al. | 128/200.16 |
| 5,865,171 A | * | 2/1999 | Cinquin | 128/200.16 |
| 6,152,383 A | * | 11/2000 | Chen | 239/102.2 |

FOREIGN PATENT DOCUMENTS

EP  0 619 761 B1  11/1992

* cited by examiner

Primary Examiner—Henry C. Yuen
Assistant Examiner—Dinh Q. Nguyen
(74) Attorney, Agent, or Firm—McGlew and Tuttle, P.C.

(57) ABSTRACT

An ultrasonic atomizer is provided with an ultrasonic converter (2) with frequency-dependent impedance characteristic. A driver system is provided (1) for generating driver signals for the ultrasound converter (2) such that while the device can be handled in a simple manner, the liquid to be applied is atomized optimally. The driver system (1) is connected such that a frequency set value with minimal driver current is sought immediately after the ultrasonic atomizer is put into operation by varying the frequency of the current signal.

20 Claims, 5 Drawing Sheets

ULTRASONIC ATOMIZER

FIELD OF THE INVENTION

Figure 1:
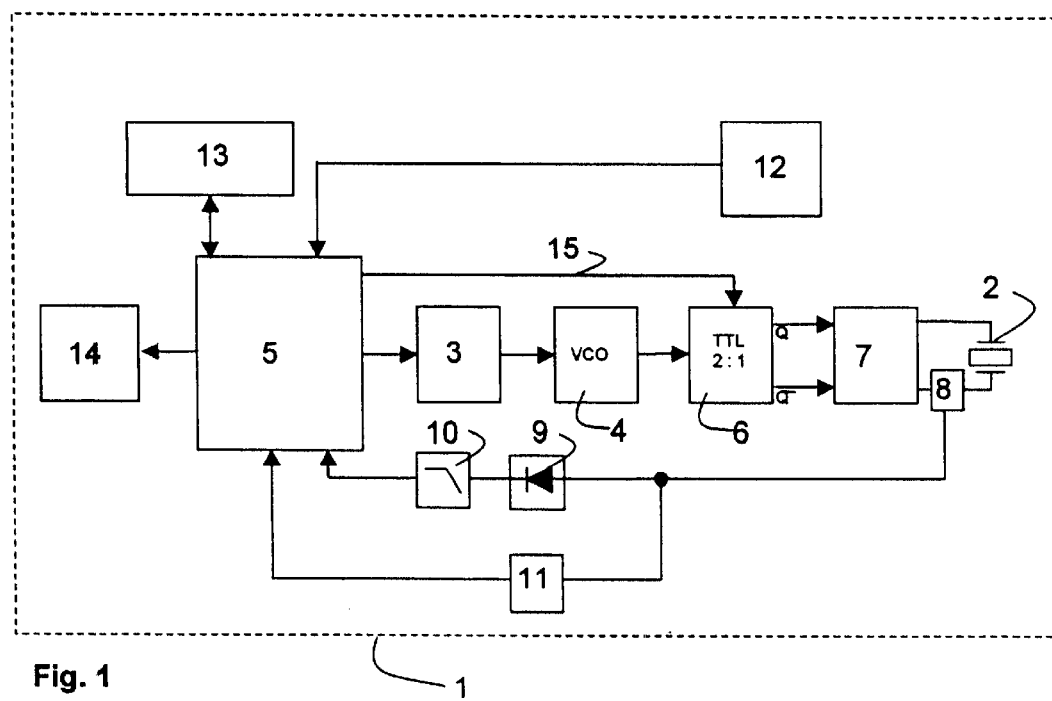

The present invention pertains to an ultrasonic atomizer with an ultrasound converter with frequency-dependent impedance characteristic and with a driver system for generating driver signals, especially a driver current for the ultrasound converter, wherein the driver system is used to excite the ultrasound converter with minimal driver current in a range of its counterresonance frequency and to a process for controlling the driver system in an ultrasonic atomizer.

BACKGROUND OF THE INVENTION

An ultrasonic atomizer of this type has been known from EP 619 761 B1. The prior-art ultrasonic atomizer is operated at its counterresonance frequency with the goal of reaching a good atomizer output at the lowest possible power supply. For optimal atomization of the liquid, the driver system of the ultrasound converter is designed such that the frequency of the driver current is adjusted in the course of the atomization in order to maintain the operation at an optimal frequency. To do so, the driver current flowing through the ultrasound converter is measured continuously and minimized by frequency variation. The frequency value of the driver current at the end of the atomization process is used as the start value for the next atomization.

The drawback of the prior-art ultrasonic atomizer is that when the ultrasonic atomizer is again put into operation, a frequency that deviates from the original setting may be necessary for good atomization because of thermal effects or a change of the liquid to be atomized. If the atomizer frequency is set unfavorably, it is also possible that the ultrasound converter will not perform any vibrations and atomization of the liquid will not take place at all.

SUMMARY AND OBJECTS OF THE INVENTION

The primary object of the present invention is to provide an improved ultrasonic atomizer such that the liquid to be atomized will be atomized optimally with simple handling of the device and to provide a process for controlling the ultrasonic atomizer.

According to the invention, an ultrasonic atomizer with a ultrasound converter with frequency-dependent impedance characteristic and with a driver system for generating driver signals, particularly a driver current for the ultrasound converter. The ultrasound converter is connected such that it receives the driver signals and performs vibrations in a liquid to be atomized. The driver system is used to excite the ultrasound converter with minimal driver current in a range of its counterresonance frequency. The driver system is connected such that a frequency set value with minimal driver current is sought immediately after putting the ultrasonic atomizer into operation by varying the frequency of the driver signal.

According to another aspect of the invention, a process is provided for controlling a driver system in an ultrasonic atomizer, which generates driver signals, especially driver currents, for an ultrasound converter with frequency-dependent impedance characteristic. The ultrasound converter is connected such that it receives the driver signals and performs vibrations in a liquid to be atomized. The driver system is used to excite the ultrasound converter in a range of its counterresonance frequency with minimal driver current. A frequency set value with minimal driver current is sought immediately after putting into operation by varying the frequency of the driver signal.

The advantage of the present invention is essentially that the frequency of the driver current is changed in the region of the counterresonance frequency immediately after putting the ultrasonic atomizer into operation in order to seek the minimum of the driver current. The frequency at which the driver current assumes its minimum is used as the frequency set value for the driver current. Since previous set values are not used, but a favorable frequency is determined for the atomization immediately after putting into operation, the atomizer output can be fully exploited from the beginning.

It is particularly advantageous to seek not only the minimum of the driver current as a criterion for the frequency of the driver current to be set, but to also consider its waviness. The waviness of the driver current is correlated with the quality of the atomization, and good atomization is achieved in case of high waviness of the driver current. Since it may happen that a plurality of minima of the driver current will occur in the frequency range being investigated, the minimum of the driver current at which the highest waviness of the current occurs is selected for the atomization. The waviness of the current is defined as the variation of the driver current around a mean value. The measured waviness signal is determined as the sum of the differences of consecutive measured current values. About 10 to 100 measured current values are evaluated for this. It is advantageous in this connection to preset limit values for both the amplitude of the driver current and the measured waviness signal. The operating conditions for the ultrasonic atomizer are optimal if the driver current is below a predetermined, first limit value and the measured waviness signal exceeds a predetermined, second limit value, because good fountain formation, which leads to a fine, floating aerosol, becomes established in the liquid being atomized at a high measured waviness signal of the driver current.

It is especially advantageous to change the frequency of the driver current in different increments. It is useful to increase the frequency with a first, large frequency increment and to measure the driver current beginning from a start value below the counterresonance frequency to an end value above the counterresonance frequency. Since there is a bandwidth of about 200 kHz between the start value and the end value, the first frequency increment is about 10 kHz to 30 kHz.

The frequency variation with a large increment offers the advantage that longer operation at high driver current values is avoided. The measurement takes place such that a corresponding driver current measured value is determined for each frequency and a minimal, first driver current is determined by comparison with a previous driver current measured value. A frequency variation is then performed around the first minimal driver current with a second frequency increment, and a second minimal driver current is determined in the same manner. The frequency belonging to the second minimal driver current is used as a frequency set value for the ultrasound converter. The frequency variation around the first minimal driver current is carried out with a span of 20 kHz downward and upward with an increment of 1 kHz. It is also possible to begin with a start value above the counterresonance frequency and to perform the frequency variation to an end value below the counterresonance frequency.

In processing the driver current measured values, it is necessary to measure each current value several times, e.g., a hundred times, and to form mean values, because errors could otherwise occur due to stochastic variations.

The ultrasound converter is directly connected to a storage tank accommodating the liquid to be atomized. The electric connection between the ultrasound converter and the driver system is advantageously effected via contact surfaces and the contact tongues touching the contact surfaces, the contact surfaces being arranged on the ultrasound converter and the contact tongues on the driver system. However, it is also possible, the other way around, to provide the ultrasound converter with contact tongues and to arrange the contact surfaces on the driver system. Due to the electrical connection between the driver system and the ultrasound converter proposed according to the present invention, it is possible to separate the two parts in a simple manner.

The ultrasound converter is advantageously fastened to the storage tank by means of an elastic bonded joint. On the one hand, a liquid-tight connection is established by the elastic bonded joint between the two components, and, on the other hand, different thermal expansions, which occur, e.g., during autoclaving, can be compensated. To center the storage tank in relation to the driver system and consequently to align the contact tongues with the contact surfaces, the bottom part of the storage tank, at which the ultrasound converter is located, is designed such that it can be plugged into a mount located on the driver system. The mount is advantageously connected to the supply unit accommodating the driver system in one piece.

An atomizer housing, into which the storage tank can be pushed together with the ultrasound converter, is advantageously provided, and the atomizer housing is closed on the underside with a supply unit, which contains the driver system. The atomizer housing and the supply unit are held together by means of a bayonet catch. The connection can be released by rotating the atomizer housing by a small amount in relation to the supply unit in order to remove the storage tank and the ultrasound converter. On its top side, the atomizer housing has connections for breathing gas tubes, with which breathing gas is introduced into the atomizer housing, on the one hand, and breathing gas enriched with the atomized liquid is sent to a user, on the other hand.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 1 is a schematic view showing a driver system for generating driver signals for an ultrasound converter;

FIG. 2 is a diagrammatic view showing an example of the driver current over time;

FIG. 3 is a diagrammatic view showing the dependence of the driver current on the frequency based on the example of the frequency tuning performed at the beginning of the operation;

FIG. 4 is a sectional schematic view showing a design of an ultrasonic atomizer;

FIG. 5 is a broken away sectional view of the connection area between the ultrasound converter and the storage tank; and FIG. 6 is a sectional view of the connection area between the ultrasound converter and the driver system.

DESCRIPTION OF THE PREFERRED EMBODIMENT

Referring to the drawings in particular, FIG. 1 schematically shows a driver system 1 for generating driver signals for an ultrasound converter 2. An oscillator 4 in the form of a so-called "Voltage-Controlled Oscillator" (VCO), driven by a d.c. power source 3, generates a digital signal with twice the needed ultrasound frequency. The d.c. power source 3 is driven for this by a microprocessor 5 with a pulse-pause-modulated d.c. voltage signal. The frequency is halved in a divider 6 arranged downstream of the oscillator 4, and two symmetrical driver signals $Q$ and $\bar{Q}$ are generated for a driver stage 7. The driver signals $Q$ and $\bar{Q}$ can be stopped or released via a control line 15 between the divider 6 and the microprocessor 5. This possibility of intervention is used for the pulse-pause modulation of the effective atomizer output without affecting the atomization amplitude proper or the frequency generation. The driver stage 7 generates the driver signal in the form of a driver current flowing through the ultrasound converter 2. A measured voltage proportional to the driver current is tapped from a measuring shunt 8. The measured voltage is demodulated with a rectifier 9, smoothed with a low-pass filter 10 and then sent as a controlled variable for the d.c. voltage signal to the microprocessor 5. In addition to the amplitude of the driver current, its waviness is evaluated with a waviness detector 11. The waviness detector 11 sends a measured waviness signal to the microprocessor 5. Via a thermistor 12, the microprocessor 5 receives a feedback on the temperature of the ultrasound converter 2 and on the temperature of the power transistors in the driver stage 7. All setting, measured and limit values are stored in a memory 13 connected to the microprocessor 5 and can be fed into the microprocessor 5 when needed. Bidirectional communication with the peripheral devices, not shown in FIG. 1, is possible via interface 14. Such a peripheral device may be, e.g., a respirator, not shown in FIG. 1, which receives both control and status reports from the driver system I and sends corresponding reports to the driver system 1. It is thus possible to drive the driver system 1 from the respirator such that atomization takes place only during the inspiration phase.

Optimal atomization of the liquid to be applied is achieved in the region of the counterresonance frequency of the ultrasound converter 2. The counterresonance frequency depends on the design of the ultrasound converter and the height of the liquid column present above the ultrasound converter 2. The working point of the ultrasound converter 2, i.e., the frequency set value at which a minimal driver current becomes established, must be determined anew when preset limit values for the driver current are exceeded.

In addition to the amplitude of the driver current, the measured waviness signals delivered by the waviness detector 11 are analyzed at different frequency settings. It was found that the piezoceramic of the ultrasound converter 2 may have a plurality of current minima in the frequency range investigated. The measured waviness signal is used to decide which of these minima is the minimum of the driver current that is optimal for the atomization of the liquid. Experiments have shown that the measured waviness signal increases in the case of a visibly good fountain formation of the liquid, while it decreases if there is no fountain formation. Good fountain formation and consequently good atomization of the liquid are associated with high waviness of the driver current. Therefore, the driver current minimum with the highest measured waviness signal is selected if a plurality of driver current minima are present. A value at which the driver current is below a predetermined first limit value and the measured waviness signal exceeds a predetermined second limit value is selected as the frequency set value for the driver current. The limit value comparisons are performed in the microprocessor 5.

To achieve satisfactory start-up of the atomization, the frequency variation of the driver current is performed according to the present invention immediately after putting into operation by seeking a first minimal driver current first with a large frequency increment beginning from a start value below the counterresonance frequency to an end value above the counterresonance frequency. The counterresonance frequency of the ultrasound converter 2 used is typically in a range between 1.75 MHz and 1.8 MHz. A frequency of about 1.7 MHz is then a suitable start value and the end value is about 1.9 MHz. The frequency increment is about 10 kHz. A second frequency variation is then performed with an increment of about 1 kHz symmetrically around the first minimal driver current with a span of 20 kHz. A second minimal driver current is determined by comparing a driver current measured value with a previous driver current measured value. The frequency belonging to the second minimal driver current is used as a frequency set value for the oscillator 4 and consequently for the ultrasound converter 2. Because of the dispersion of the driver current measured values, it is necessary to measure the driver current several times, e.g., a hundred times, at each frequency, and to form a mean value. The mean value is likewise formed in the microprocessor 5.

Figure 2:
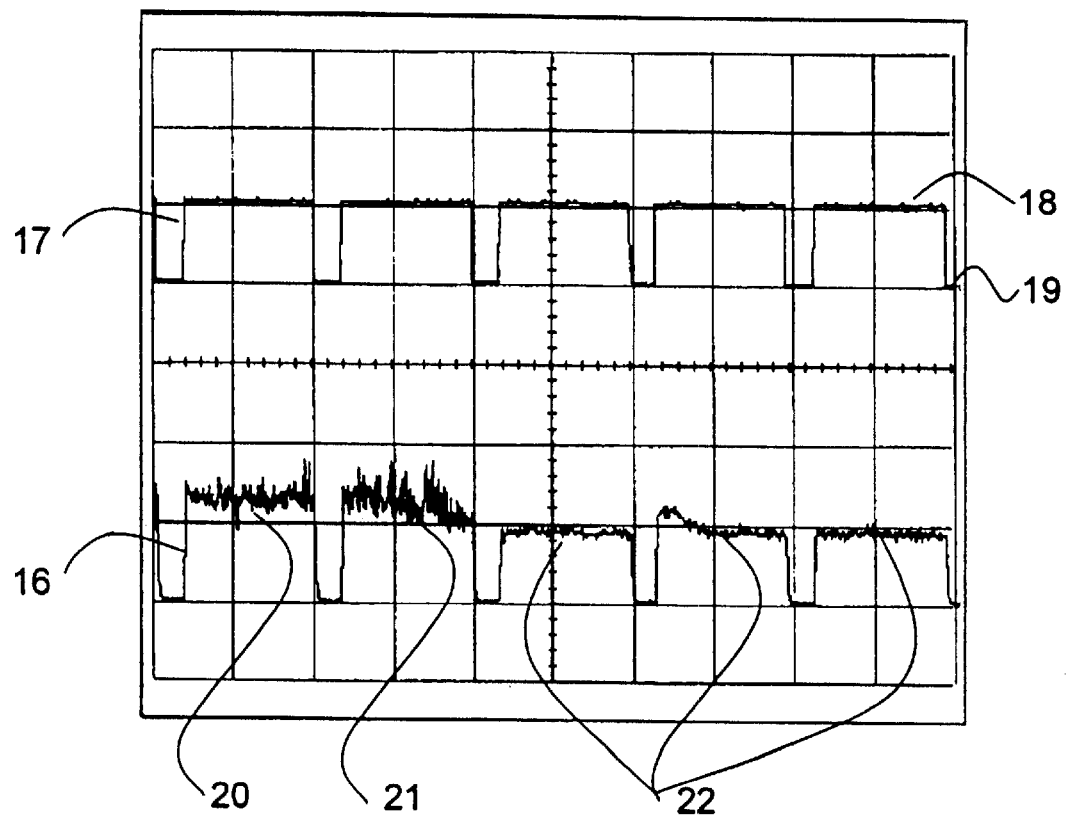

FIG. 2 shows examples of the driver current over time (curve 16). Curve 17 shows the timing signal, which is sent to the divider via the control line 15 and with which the ultrasound converter 2 is switched on and off, as a function of the time. The upper voltage value 18 corresponds to the ultrasound converter 2 switched on and the lower voltage value 19 corresponds to the ultrasound converter 2 switched off.

Section 20 shows an intended waviness, which becomes established during the atomization of a liquid. Section 21 shows a superproportional waviness, which is caused by the formation of droplets during the atomization. No waviness of the driver current is present in sections 22, because the liquid was completely atomized. The measured waviness signal is therefore also an indicator of the end of the atomization.

Figure 3:
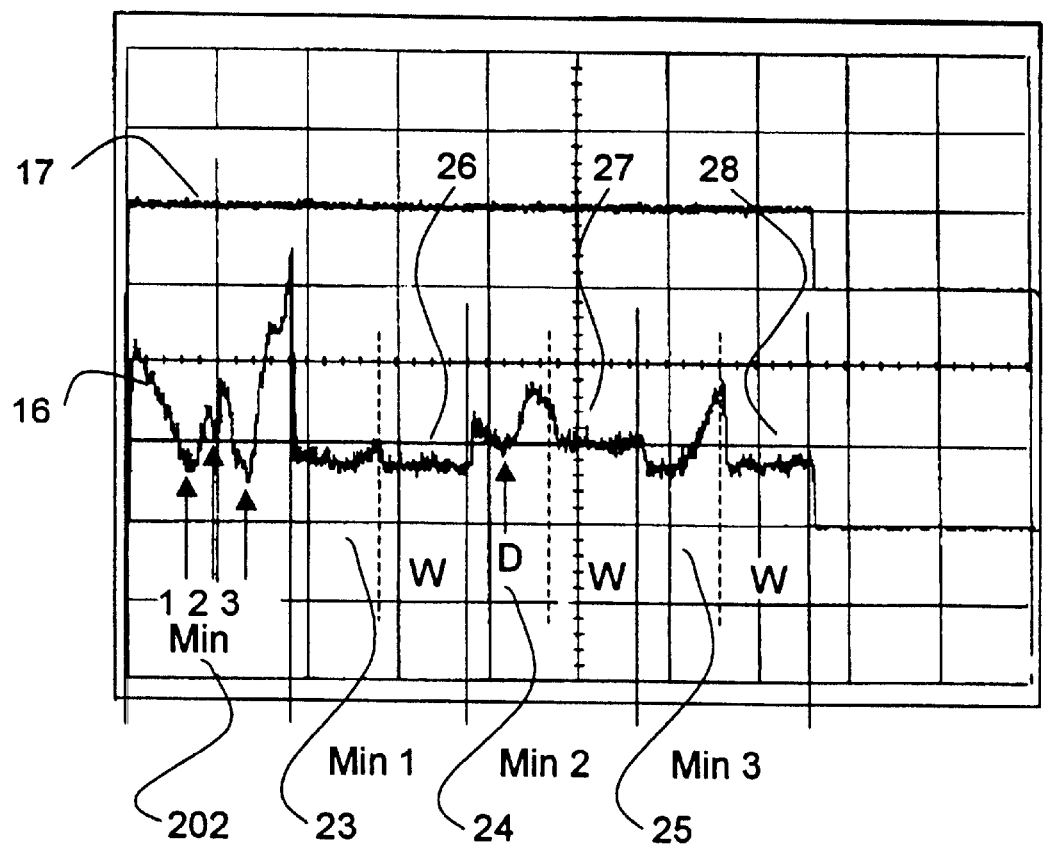

FIG. 3 illustrates the driver current 16 as a function of the frequency set on the oscillator 4. The result obtained with frequency tuning between 1.7 MHz and 1.9 MHz with an increment of 20 kHz is shown in section 202. There are three minima for the driver current here, namely, Min 1, Min 2 and Min 3. With a span of 20 kHz each, further minima are sought symmetrically around these minima Min 1, Min 2 and Min 3 with an increment of 1 kHz. The results of the frequency variations in the region of the minima Min 1, Min 2 and Min 3 are illustrated in sections 23, 24, 25. The corresponding measured waviness signals W are compared in sections 26, 27, 28. The frequency D in section 24 is selected in the range of minimum 2 as the optimal frequency set value, because the measured waviness signal, in section 27, is bigger here than in sections 26 and 28.

Figure 4:
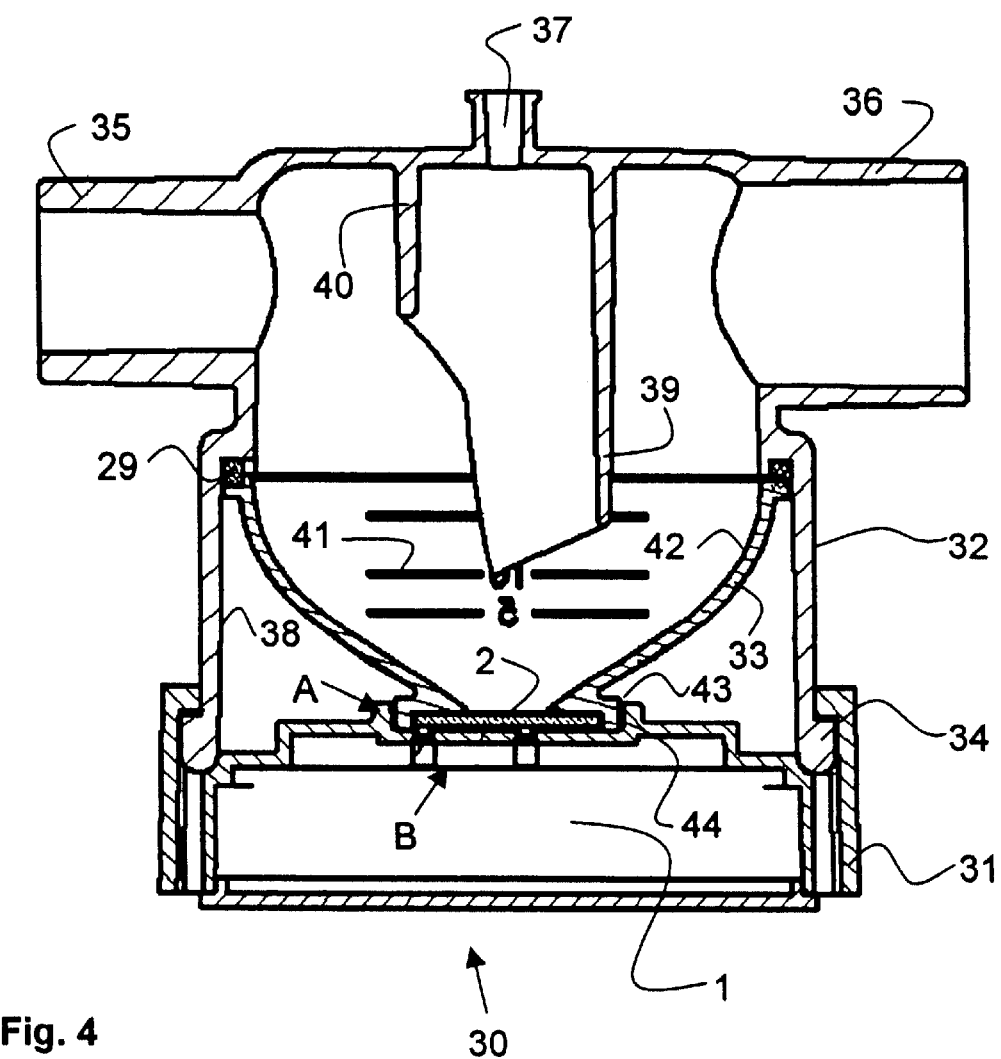

FIG. 4 schematically shows the longitudinal section of an ultrasonic atomizer 30. The ultrasonic atomizer 30 comprises a supply unit 31 accommodating the driver system 1, an atomizer housing 32, and a storage tank 33 containing the ultrasound converter 2. The atomizer housing 32 and the supply unit 31 are connected to one another via a bayonet catch 34, so that the electronic components can be separated from the atomizer housing 32 and the storage tank 33 accommodating the liquid by a quarter turn. The atomizer housing 32 has connection cones 35, 36, with which the gas connections to the anesthesia devices or respirators, not shown in the figures, can be established. Furthermore, the atomizer housing 32 has a filling adapter 37, via which the liquid to be atomized can be filled into the storage tank 33. The storage tank 33 is pushed with its open end into a hole 38 in the atomizer housing 32 and is sealed with an O ring 29, so that a gas space, through which breathing gas flows, is formed by the connection cones 35, 36 and the interior space of the storage tank 33. A protective wall 39 extending into the storage tank 33 is present around the filling adapted to prevent a water column, which is not shown in FIG. 4 and is formed during the ultrasonic atomization, from being entrained by the gas flow flowing between the connection cones 35, 36. On the side 40 facing away from the flow, the protective wall 39 is cut up to enable the aerosol to be discharged there. Liquid particles collecting at the protective wall 39 can flow back into the storage tank 33 unhindered.

The storage tank 33, which is used to store and atomize the liquid, consists, like the atomizer housing 32, of a transparent plastic suitable for autoclaving. The storage tank 33 can hold about 20 mL of liquid. To estimate the amount of liquid, a scale 41 is arranged on the wall of the storage tank 33. The storage tank 33 comprises an elliptical upper part 42 and a circular bottom part 43, into which the ultrasound converter 2 is placed. In the area of the bottom part 43, the supply unit 31 has a mount 44, into which the bottom part 43 can be pushed. The 20 storage tank 33 is centered in relation to the supply unit 31 by the bottom part 43 and the mount 44 fitting one another.

Figure 5:
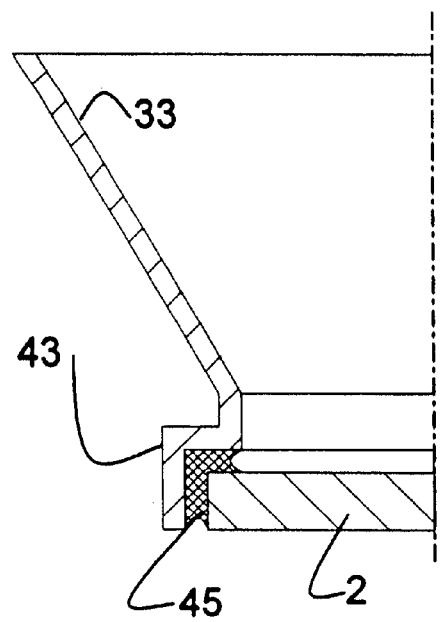

FIG. 5 shows detail A according to FIG. 4 in the connection area between the bottom part 43 of the storage tank 33 and the ultrasound converter 2. Identical components are designated by the same reference numbers as in FIG. 4. An elastic bonded joint 45 consisting of a silicone material, which also seals the ultrasound converter 2 against the storage tank 33 at the same time, is provided for the stress-free fastening of the ultrasound converter 2 in the area of the bottom part 43 of the storage tank 33. Stresses may develop, e.g., during the autoclaving, because the material of the storage tank 33 and the ultrasound converter 2 have different coefficients of thermal expansion.

Figure 6:
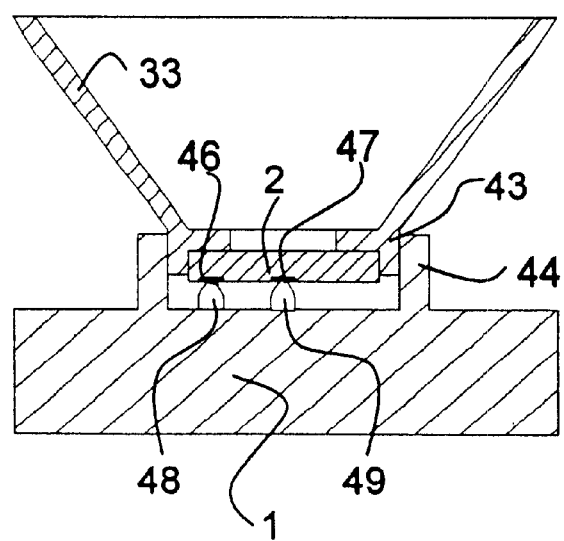

FIG. 6 shows detail B according to FIG. 4 in the connection area between the driver system 1 and the ultrasound converter 2. Identical components are designated by the same reference numbers as in FIG. 4. Contact surfaces 46, 47 are arranged on the ultrasound converter 2 and contact tongues 48, 49 are arranged on the driver system 1 for the electrical connection of the ultrasound converter 2 to the driver system 1. The contact tongues 48, 49 are centered in relation to the contact surfaces 46, 47 by the plug-type connection between the bottom part 43 of the storage tank 33 and the mount 44.

While a specific embodiment of the invention has been shown and described in detail to illustrate the application of the principles of the invention, it will be understood that the invention may be embodied otherwise without departing from such principles.

What is claimed is:
1. An ultrasonic atomizer, comprising:
   an ultrasound converter with a frequency-dependent impedance characteristic;
   a driver system for generating driver signals including a driver current for the ultrasound converter, the ultrasound converter being connected such that it receives the driver signals and performs vibrations in a liquid to be atomized, said driver system exciting the ultrasound converter with minimal driver current in a range of its counterresonance frequency, said driver system provid- ing a varied frequency of the driver signal and determining a plurality of relative driver current minimums, said driver system including a waviness detector determining a waviness of the driver current, said driver system selecting a frequency of one of said relative driver current minimums with a maximum said waviness as an operating frequency of the ultrasound converter.

2. An ultrasonic atomizer in accordance with claim 1, wherein the driver system is connected such that the provided varied frequency of the driver signal, begins from a start value below the counterresonance frequency to an end value above the counterresonance frequency and the frequency is increased with a first frequency increment, a corresponding driver current is determined for each frequency, and a minimal first driver current is sought by comparing a driver current measured value with a previous driver current measured value, and that a second minimal driver current is determined in a range around the first minimal driver current by comparing a driver current measured value with a previous driver current measured value by reducing the first frequency increment to a second frequency increment, and the frequency belonging to the second minimal driver current is used as the frequency set value.

3. An ultrasonic atomizer in accordance with claim 2, wherein the start value is above the counterresonance frequency and the end value is below the counterresonance frequency and that the frequency is reduced beginning from the start value with the first frequency increment.

4. An ultrasonic atomizer in accordance with claim 2, wherein the second frequency increment is set at a percentage between 5% and 20% of the first frequency increment.

5. An ultrasonic atomizer in accordance with claim 2, wherein the first frequency increment is between 10 kHz and 30 kHz.

6. An ultrasonic atomizer in accordance with claim 1, further comprising: a supply unit accommodating the driver system; and
a storage tank wherein the ultrasound converter is connected to the storage tank accommodating the liquid to be atomized, and that together with the storage tank, the ultrasound converter being connected to the supply unit such that the electrical connection between the supply unit and the ultrasound converter is formed by contact surfaces and contact tongues touching the contact surfaces.

7. An ultrasonic atomizer in accordance with claim 6, wherein the ultrasound converter is fastened to a bottom part of the storage tank with a elastic bonded joint.

8. An ultrasonic atomizer in accordance with claim 7, wherein the bottom part of the storage tank located in the area of the ultrasound converter is designed as a bottom part that can be plugged into a mount on the supply unit.

9. An ultrasonic atomizer in accordance with claim 6, wherein said contact surfaces are arranged on the ultrasound converter and the contact tongues are arranged on the supply unit.

10. An ultrasonic atomizer in accordance with claim 6, wherein the contact surfaces are provided on the supply unit and the contact tongues on the ultrasound converter.

11. An ultrasonic atomizer in accordance with claim 6, wherein an upper part of the storage tank has an elliptical, round or rectangular cross-sectional area.

12. An ultrasonic atomizer in accordance with claim 6, further comprising an atomizer housing accommodating said storage tank and said supply unit, said atomizer housing having a top side with connections for breathing tubes and having an underside is able to be connected to the supply unit, wherein the storage tank is designed, together with the ultrasound converter, to be able to be pushed into a mounting hole of the atomizer housing.

13. An ultrasonic atomizer in accordance with claim 1, wherein:
said driver system begins varying of the frequency immediately after putting the ultrasonic atomizer into operation from a start value below the counterresonance frequency to an end value above the counterresonance frequency.

14. A process for controlling a driver system in an ultrasonic atomizer, the process comprising the steps of:
generating driver signals including driver currents, for a ultrasound converter with frequency-dependent impedance characteristic, wherein the ultrasound converter is connected such that it receives the driver signals and performs vibrations in a liquid to be atomized;
using the driver system to excite the ultrasound converter in a range of frequencies;
measuring a driver current of said driver signal over said range of frequencies;
determining a plurality of relative minimums of said driver current over said range of frequencies;
measuring a waviness of said driver current over said range of frequencies;
selecting a frequency of one of said relative minimums with a maximum said waviness as an operating frequency of the ultrasound converter.

15. A process in accordance with claim 14, wherein an initial frequency in said range of frequencies is increased by a first frequency increment beginning from a start value below a counterresonance frequency to an end value above the counterresonance frequency, a corresponding driver current amplitude is determined at each frequency, a minimal first driver current is sought by comparing a driver current measured value with a previous driver current measured valued, a second minimal driver current is determined in a range around the first minimal driver current by comparing a driver current measured value with a previous driver current measured value by reducing the first frequency increment to a second frequency increment, and a frequency belonging to the second minimal driver current is used as the frequency set value.

16. A process in accordance with claim 15, wherein a value above the counterresonance frequency is used as the start value and a frequency below the counterresonance frequency is used as the end value, and the frequency is reduced beginning from the start value with the first frequency increment.

17. A process in accordance with claim 15, wherein a value between 10 kHz and 30 kHz is used as the first frequency increment.

18. A process in accordance with claim 15, wherein the second frequency increment is set at a percentage between 5% and 20% of the first frequency increment.

19. A process in accordance with claim 14, wherein:
said using the driver system to excite the ultrasound converter in a range of frequencies begins immediately after putting the ultrasonic atomizer into operation from a start value below a counterresonance frequency to an end value above the counterresonance frequency.

20. A process for controlling an ultrasonic atomizer, the process comprising the steps of:
providing an ultrasound converter with a frequency-dependent impedance characteristic;

driving the ultrasound converter with a driver signal;
measuring a driver current of said driver signal;
varying a frequency of said driver signal;
determining a plurality of relative minimums of said driver current with respect to the frequency of said driver signal;
measuring a waviness of said driver current;
selecting a frequency of one of said relative minimums with a maximum said waviness as an operating frequency of the ultrasound converter.

* * * * *